United States Patent [19]

Heeres et al.

[11] 4,338,327
[45] Jul. 6, 1982

[54] SUBSTITUTED 1-(2-ARYL-1,3-DIOXOLAN-2-YLMETHYL)-1H-1,2,4-TRIAZOLES

[75] Inventors: Jan Heeres, Vosselaar; Leo Backx, Arendonk, both of Belgium; Adolf Hubele, Magden; Robert Nyfeler, Basel, both of Switzerland

[73] Assignee: Janssen Pharmaceutica, N.V., Beerse, Belgium

[21] Appl. No.: 53,640

[22] Filed: Jun. 29, 1979

Related U.S. Application Data

[63] Continuation-in-part of Ser. No. 949,329, Oct. 6, 1978, abandoned.

[51] Int. Cl.³ .................. C07D 405/06; A61K 31/40
[52] U.S. Cl. .................................. 424/269; 548/101; 548/106; 548/107; 548/262
[58] Field of Search ................ 424/269; 548/262, 101, 548/106, 107

[56] References Cited

U.S. PATENT DOCUMENTS 4,223,036  9/1980  Heeres et al. ..................... 548/262
4,267,179  3/1981  Heeres et al. ..................... 548/262

Primary Examiner—Donald G. Daus
Assistant Examiner—James H. Turnipseed
Attorney, Agent, or Firm—Geoffrey G. Dellenbaugh

[57] ABSTRACT

Novel 1-(2-aryl-1,3-dioxolan-2-ylmethyl)-1H-1,2,4-triazoles wherein the 1,3-dioxolane ring is substituted in the 4-position which are useful for the protection of plants and plant products against fungal attack.

11 Claims, No Drawings

SUBSTITUTED 1-(2-ARYL-1,3-DIOXOLAN-2-YLMETHYL)-1H-1,2,4-TRIAZOLES

CROSS-REFERENCE TO RELATED APPLICATIONS

This is a continuation in part of our copending application Ser. No. 949,329, filed Oct. 6, 1978, now abandoned.

BACKGROUND OF THE INVENTION

A number of 1-(2-aryl-1,3-dioxolan-2-ylmethyl)-1H-imidazoles having different substituents, including oxymethyl and thiomethyl groups, in the 4-position of the dioxolane moiety are described in the following references:

U.S. Pat. No. 3,936,470;
U.S. Pat. No. 4,101,666;
U.S. Pat. No. 4,101,665;
U.S. Pat. No. 4,101,664; and
Belg. Pat. No. 837,831.

The compounds of the present invention differ from the foregoing essentially by the replacement of the 1H-imidazole group of the prior art compounds by a 1H-1,2,4-triazole group.

In Belg. Pat. Nos. 863,437 and 863,382 there are described 1-(2-aryl-1,3-dioxolan-2-ylmethyl)-1H-1,2,4-triazoles bearing in the 4-position of the 1,3-dioxolane moiety an aryloxymethyl group wherein the aryl group is further substituted with an aliphatic or alicyclic amine group or with a nitrogen-containing heteroaromatic ring.

The compounds of this invention differ therefrom essentially by the nature of the $R^4$-oxymethyl or $R^4$-thiomethyl substituent attached to the 4-position of said 1,3-dioxolane moiety.

DESCRIPTION OF THE INVENTION

This invention relates to novel 1H-1,2,4-triazole derivatives having the formula (I)

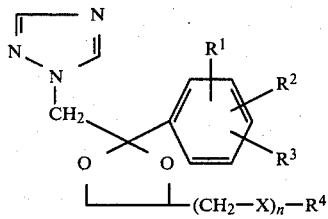

and the phytopharmaceutically acceptable acid addition salts, metal salt complexes and stereochemically isomeric forms thereof, wherein $R^1$, $R^2$ and $R^3$ are each independently selected from the group consisting of hydrogen, lower alkyl, lower alkyloxy, halo, nitro, cyano and trifluoromethyl;
n is the integer 0 or 1;
X is a member selected from the group consisting of O and S; and
$R^4$ is a member selected from the group consisting of alkyl, mono-, di- and trihalo-alkyl, lower alkyloxy-lower alkyl, mono-, di- and trihalo-lower alkyloxy-lower alkyl, lower alkenyl, 2-propynyl, 3-halo-2-propynyl, cycloalkyl, aryl, aryl-lower alkyl and aryl-lower alkenyl, wherein said aryl is selected from the group consisting of phenyl and substituted phenyl, said substituted phenyl having from 1 to 3 substituents each independently selected from the group consisting of lower alkyl, lower alkyloxy, halo, nitro, cyano, trifluoromethyl, phenyl, phenyloxy and phenylthio, provided that only one of the substituents may be selected from the group consisting of phenyl, phenyloxy and phenylthio, and wherein said phenyl and the phenyl part of said phenoxy and phenylthio are optionally substituted with up to three substituents each independently selected from the group consisting of lower alkyl, lower alkyloxy, halo, nitro, cyano and trifluoromethyl, provided that when n is 0 then $R^4$ is other than alkyl.

Preferred compounds within the scope of the present invention are those wherein n is 1 and $R^4$ is a member selected from the group consisting of alkyl, lower alkyloxy lower alkyl, lower alkenyl, 2-propynyl, 3-halo-2-propynyl, aryl, aryllower alkyl and aryllower alkenyl, wherein said aryl is selected from the group consisting of phenyl and substituted phenyl having from 1 to 3 substituents each independently selected from the group consisting of lower alkyl, lower alkyloxy and halo.

As used in the foregoing and in the following definitions, the term halo is generic to fluoro, chloro, bromo and iodo; "alkyl", used as such or being part of another substituent, is meant to include straight and branched hydrocarbon radicals having from 1 to 12 carbon atoms such as, for example, ethyl, butyl, hexyl, octyl, decyl, dodecyl, 2-methylpropyl, 3-ethylpentyl, 3-methylbutyl and the like; "lower alkyl", used as such or being part of another substituent, is meant to include straight and branched hydrocarbon radicals having from 1 to 6 carbon atoms such as, for example, methyl, propyl, pentyl, 1-methylethyl, 1,1-dimethylethyl and the like; "lower alkenyl" is meant to include straight and branched alkenyl radicals having from 2 to 6 carbon atoms, wherein the saturation is preferably located at the β-position, but can also be located at the γ, δ or ε-positions, such as, for example, 2-propenyl, 2-butenyl, 3-methyl-2-butenyl and the like; and "cycloalkyl" is meant to include cyclopropyl, cyclobutyl, cyclopentyl and cyclohexyl.

The compounds of formula (I) can be prepared by the reaction of a 1H-1,2,4-triazole of the formula (II)

wherein Me is hydrogen or, preferably, a metal atom, most preferably an alkali metal atom, with a reactive ester of the formula (III)

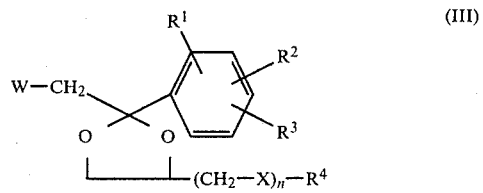

wherein $R^1$, $R^2$, $R^3$, $R^4$, n and X have the previously indicated meaning and W represents a reactive ester residue such as for example, halo, particularly chloro, bromo or iodo, or a sulfonyloxy group such as, for example, methylsulfonyloxy, 4-methylphenylsulfonyloxy and the like.

The reaction of (II) with (III) is preferably carried out in a relatively polar, reaction-inert organic solvent, such as, for example, N,N-dimethylformamide, N,N-dimethylacetamide, dimethylsulfoxide, acetonitrile, benzonitrile and the like. Such solvent can be used in combination with other reaction-inert solvents, e.g. aliphatic or aromatic hydrocarbons such as, for example, benzene, methylbenzene, dimethylbenzene, hexane, petroleumether, chlorobenzene, nitrobenzene and the like. When said W represents chloro or bromo it may be advantageous to conduct the reaction in the presence of an alkali metal iodide, such as sodium or potassium iodide, to enhance the reaction rate. Elevated temperatures of from about 30° to about 220° C., preferably from about 80° to about 170° C. are appropriate and conveniently the reaction is carried out under reflux.

When Me represents hydrogen the reaction is carried out in the presence of a base. Suitable bases which may be utilized include alkali metal oxides, hydroxides, carbonates and hydrogen carbonates as well as tertiary amines such as N,N-diethylethanamine, pyridine and the like. In view of its basic properties 1H-1,2,4-triazole, when added in excess, may be used to promote the reaction.

In these and the following preparations the reaction products may be isolated from the medium and, if necessary, further purified according to methodologies generally known in the art, such as, for example, extraction, trituration, crystallization, chromatography and the like.

An additional method of preparing the compounds of formula (I) is by the acetalization of an appropriate aroylmethyl-1H-1,2,4-triazole of formula (IV), wherein $R^1$, $R^2$ and $R^3$ have the previously defined meanings, with an appropriate diol of formula (V), wherein X, n and $R^4$ are as previously defined.

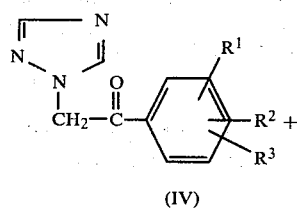

(IV)

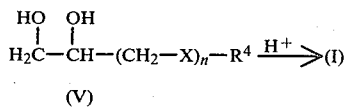

(V)

Said acetalization-reaction may be carried out following methodologies analogous to those described in the literature, e.g., for the preparation of 2-bromomethyl-2,4-diphenyl-1,3-dioxolane [Synthesis, 1974 (I), 23].

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons such as n.hexane. Alternatively the acetals of formula (I) may be derived from other cyclic- or aliphatic acetals by reacting the latter with an excess of the 1,2-diol (V), corresponding to the desired acetal.

The compounds of formula (I) wherein n is other than 0, said compounds being represented by the formula (I-a) can also be prepared by reacting an appropriate compound of formula (VI), wherein $R^1$, $R^2$, $R^3$ and X are as previously defined, with an appropriate reactive ester of formula (VII), wherein $R^4$ has the previously indicated meaning and W is a reactive ester function as previously defined, according art-known conditions of performing O-alkylations and S-alkylations with reactive esters.

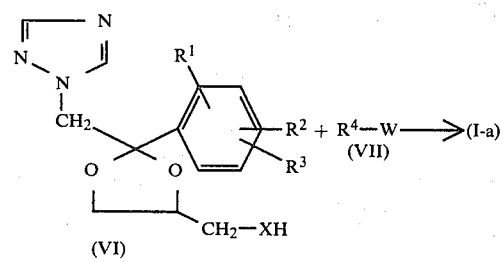

(VI)

The reaction is generally carried out in an appropriate reaction-inert organic solvent such as, for example, N,N-dimethylformamide, N,N-dimethylacetamide, hexamethylphosphoric triamide, dimethylsulfoxide, 4-methyl-2-pentanone and the like, optionally in admixture with other reaction-inert solvents such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the rate of the reaction. Otherwise it may be advantageous to first convert the compound (VI) into a metal salt thereof, preferably the sodium salt, in the usual manner, e.g., by the reaction of (VI) with metal bases such as sodium hydride, sodium hydroxide and the like, and to use thereafter said metal salt in the reaction with (VII).

Somewhat elevated temperatures are appropriate to enhance the reaction rate and most preferably the reaction is carried out at from about 80° C. to about 130° C.

Those compounds of formula (I-a) wherein $R^4$ is different from mono-, di- and trihalo-alkyl and different from mono-, di- and trihalo-lower alkyloxy-alkyl, said $R^4$ being represented by $R^{4'}$ and said compounds being represented by the formula (I-a-1), may still be prepared by the reaction of an appropriate reactive ester of formula (VIII), wherein $R^1$, $R^2$, $R^3$ and W have the previously defined meanings, with an appropriate compound of formula (IX), wherein X is as previously defined, according art-known conditions of performing O-alkylations and S-alkylations with reactive esters as described hereabove for the preparation of compounds (I) starting from (VI) and (VII).

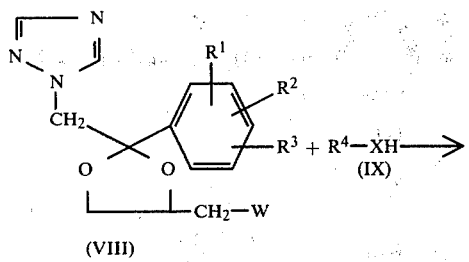

(VIII)

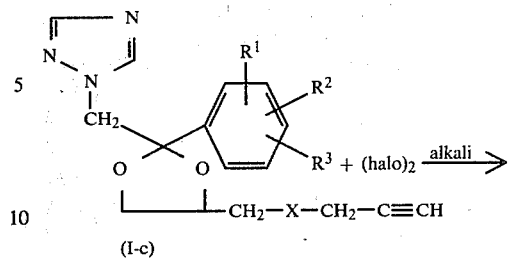

(I-c)

(I-a-1)

(I-b)

The compounds of formula (I) wherein R⁴ is alkyl and X is O, said compounds being represented by the formula (I-a-2), may still be prepared by the condensation-reaction of (VI) wherein X is O, said compound being represented by (VI-1), with an alcohol of formula (X).

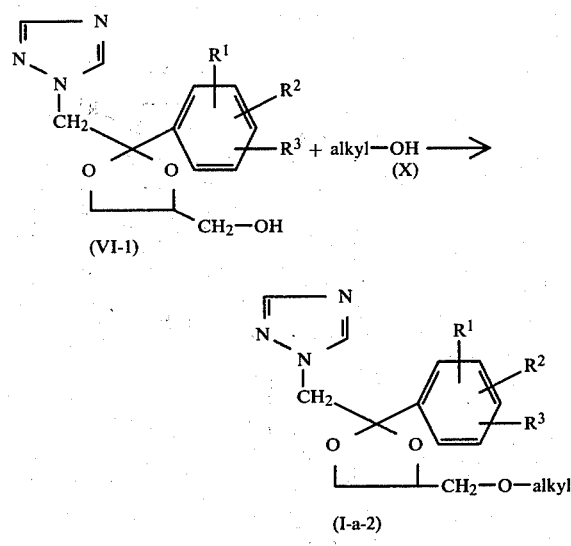

(I-a-2)

Said condensation reaction may be carried out by refluxing the reactants together under azeotropic water removal in an appropriate organic solvent such as, for example, an aromatic hydrocarbon, e.g., benzene, methylbenzene, dimethylbenzene and the like, a saturated hydrocarbon, e.g., n. hexane or in the alkanol itself, in the presence of an appropriate strong acid such as, for example, 4-methylbenzenesulfonic acid.

The compounds of formula (I) wherein R⁴ is 3-halo-2-propynyl, said compounds being represented by formula (I-b), can be prepared starting from the corresponding 2-propynyl derivative (I-c) by replacing the acidic hydrogen of the latter with an appropriate halo-atom, preferably chloro, bromo or iodo, most preferably bromo or iodo.

The foregoing halogenation reaction may be carried out by stirring the reactants together in an appropriate reaction-inert solvent such as, for example, a lower alkanol, e.g., methanol, ethanol and the like, in the presence of at least one equivalent alkali such as, for example, a metal hydroxide, e.g., sodium hydroxide, and the like.

Suitable salt-forming acids are respectively well-tolerated by plants or physiologically acceptable, such as, for example, an inorganic acid such as hydrohalic acid, i.e., hydrochloric, hydrobromic, or hydroiodic; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic methanesulfonic, ethanesulfonic, hydroxyethanesulfonic, 4-methylbenzenesulfonic, 2-hydroxybenzoic, 4-amino-2-hydroxybenzoic, 2-phenoxybenzoic, 2-acetyloxybenzoic, 2,4-hexadienoic or 1,5-naphthalenedicarboxylic acid.

Metal salt complexes of formula (I) may be obtained by the complexation-reaction of a triazole of formula (I) with an organic or inorganic metal salt such as, for example, hydrohalides, nitrates, sulfates, phosphates, 2,3-dihydroxybutanedioates and the like of copper, manganese, zinc, iron and the like transition metals, which may be present in each of their possible valencies.

Stoechiometrically defined metal salt complexes may be prepared by dissolving a compound of formula (I) in a water-miscible solvent (e.g. warm ethanol, methanol, 1,4-dioxane or N,N-dimethylformamide) and adding thereto an aqueous solution of the desired metal salts such as, for example, CuSO₄.5H₂O, Mn(NO₃)₂.4H₂O, FeCl₃.6H₂O and the like.

The foregoing enumerations are intended to illustrate and not to limit the scope of the present invention.

A number of the intermediates and starting materials used in the foregoing preparations are known compounds, others may be prepared according to art-known methodologies of preparing similar compounds and some of them are novel and consequently their preparation will be described hereafter.

The arylacetals of formula (III) and the α,β-diols of formula (V) are described in U.S. Pat. No. 4,101,666.

The aroylmethyl substituted 1,2,4-triazoles of formula (IV) are conveniently prepared by the reaction of a reactive ester of formula (XI), wherein $R^1$, $R^2$, $R^3$ and W are as previously described, with a 1H-1,2,4-triazole of formula (II) in an analogous manner as previously described for the preparation of the compounds (I) starting from 1H-1,2,4-triazole (II) and (III).

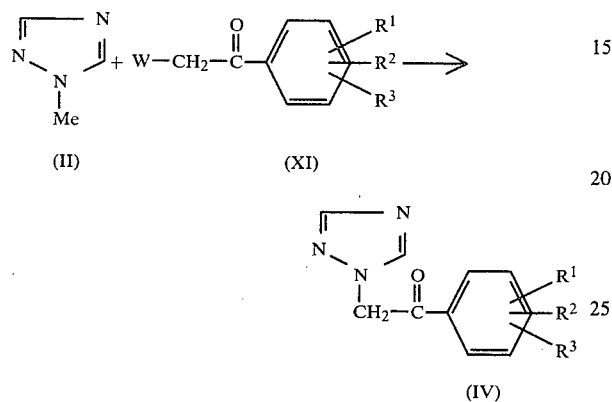

The precursor arylketones of formula (XI) are generally known and may be prepared according to known procedures as described in the literature. Bromides are, for example, easily obtained by the bromination of the corresponding 1-Ar-2-bromoethanone of formula (XII) with bromine.

The intermediates of formula (VI) and methods of preparing the same may be prepared following methods described in Belg. Pat. No. 837,831 for the preparation of the analogous imidazole derivatives.

An appropriate 1-Ar-2-haloethanone of formula (XII) is subjected to an acetalization reaction with 1,2,3-propanetriol following methodologies analogous to those described in Synthesis 1974, (I), 23.

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as n.hexane.

The thus obtained dioxolane (XIII) is then reacted with benzoyl chloride to obtain a benzoate of formula (XIV) and the latter is subsequently reacted with the 1H-1,2,4-triazole (II). Said reaction is carried out according to methodologies analogous to those previously described for the preparation of (I) starting from (II) and (III). The desired intermediates of formula (VI) wherein X is O, said intermediates being represented by (VI-1), are conveniently prepared by hydrolyzing (XV) in alkaline medium.

The foregoing reactions may be illustrated as follows:

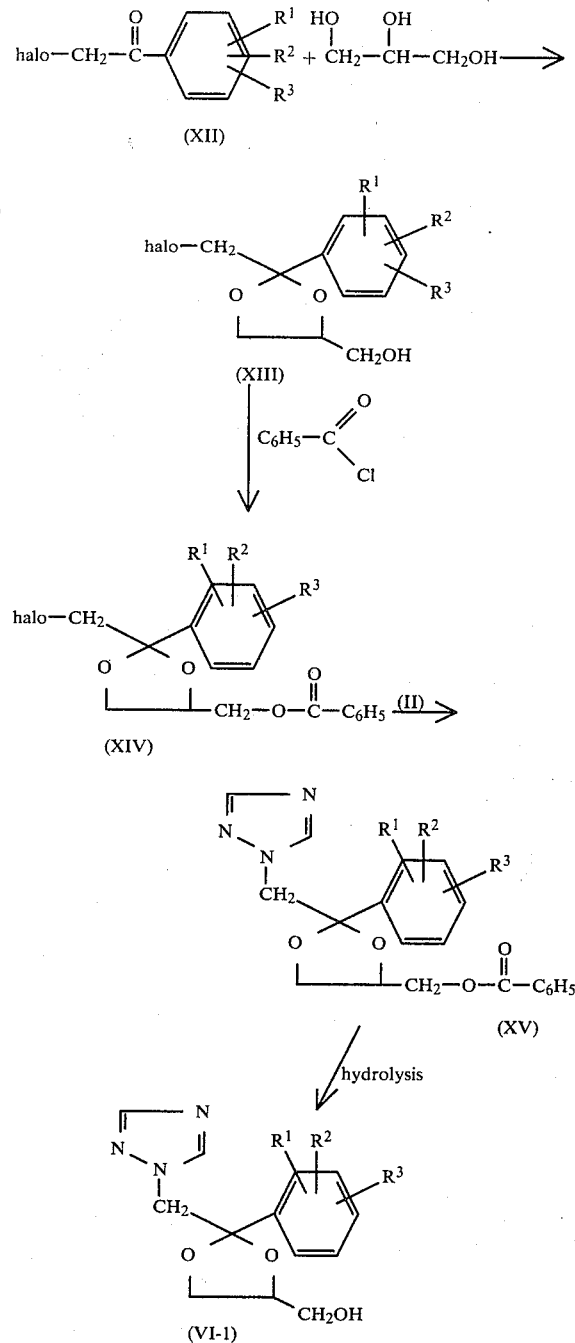

It should be noted that the benzoylation of (XIII) and the hydrolysis of the thus prepared intermediated (XV) is not mandatory. In fact, the intermediates (VI-1) can quite simply be prepared directly by the reaction of (XIII) with (II). However the insertion of said benzoylation may advantageously be employed to facilitate the separation of cis- and trans-forms of the resulting intermediates (XIV) and (XV).

The intermediates of formula (VI), wherein X is S, said intermediates being represented by (VI-2), may conveniently be prepared starting from (VI-1) following art-known methodologies for converting an alcohol into the corresponding thiol. (See Saul Patai Ed. "The Chemistry of the Thiol Group" London-New York- Sydney-Toronto, Ch. 4). In a preferred method the compounds (VI-2) are conveniently obtained by the treatment of (VI-1) with phosphorous pentasulfide.

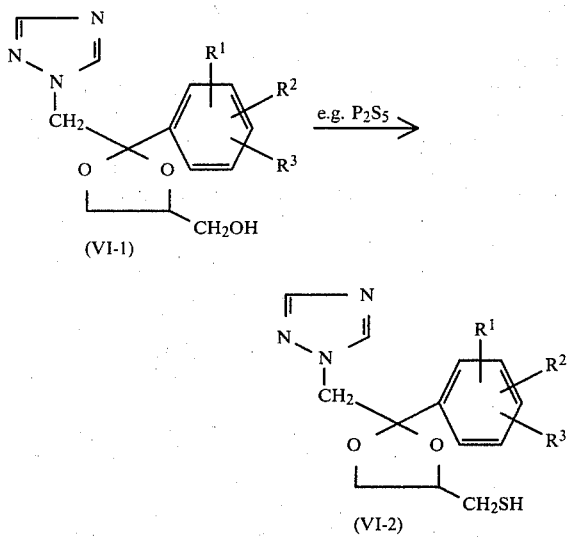

The intermediates of formula (VIII) may easily be prepared by converting the alcohol (VI-1) into a corresponding reactive ester according to methodologies generally known in the art. For example, methanesulfonates and 4-methylbenzenesulfonates are conveniently prepared by the reaction of the alcohol with methanesulfonyl chloride or 4-methylbenzenesulfonyl chloride and halides may be prepared by the reaction of the alcohol with an appropriate halogenating agent such as, for example, sulfuryl chloride, phosphor pentachloride, phosphor pentabromide, phosphoryl chloride and the like. When the reactive ester is a iodide, it is preferably prepared from the corresponding chloride or bromide by the replacement of that halogen with iodine.

From formula (I) is is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (I) and the pharmaceutically acceptable acid addition salts thereof are intended to be within the scope of this invention.

The diastereomeric racemates of (I), denoted as cis and trans forms respectively according to the rules described in C.A., 76, Index Guide, Section IV, p. 85 (1972), may be obtained separately by conventional methods. Appropriate methods which may advantageously be employed therefore include, for example, selective crystallization and chromatographic separation, e.g. column-chromatography. For a number of compounds the stereochemical configuration was experimentally determined. In the remaining cases it is conventionally agreed to designate the stereochemical form which is first isolated as "A" and the second as "B", without further reference to the actual stereochemical configuration.

Since the stereochemical configuration is already fixed in the intermediates (III), (VI) and (VIII) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

The compounds of formula (I) can be used alone or in admixture with appropriate carriers and/or additives. Appropriate carriers and additives can be solid or fluid and are generally known in the art of formulating, such as, for example, natural and regenerated mineral substances, solvents, dispersants, wetting agents, adhesives, thickners, binders or fertilizers.

The concentration of the active ingredient in commercial preparations can vary from about 0.1 to about 90%.

For their application the compounds of formula (I) can be formulated in the following composition-forms (whereby suitable concentrations of the active ingredient are indicated within brackets):

solid compositions: dusts
(up to 10%), granulates, coated granulates, impregnated granulates and homogeneous granulates, pellets (from 1 to 80%);

liquid compositions:
(a) water-dispersible concentrates: wettable powders and pastes (25–90% in commercial form, 0.01–15% in the ready for use soluion); emulsion- and solution-concentrates (10–50%; 0.01–15% in ready for use solution);
(b) solutions (0.1–20%); aerosols.

If desired, in order to extend their spectrum of activity the compounds of formula (I) may be combined with other appropriate pesticides such as, for example, fungicides, bactericides, insecticides, acaricides, herbicides, plant-growth regulators and the like. Such compositions are intended to be within the scope of the present invention.

Particularly, the compounds of formula (I) possess a very advantageous antimicrobial spectrum, rendering them useful for the protection of crops without causing undesired side-reactions. Examples of crops within the scope of this invention are the followings: cereals, maize, rice, vegetables, sugar-beet, soybeans, groundnuts, fruit-trees, ornamentals, grapevines, hops, cucurbitaceae (gherkins, cucumbers, melons), solanaceae such as potatoes, tobacco and tomatoes, as well as bananas, cocoa and rubber.

The compounds of formula (I) can be used to reduce or destroy fungal growth on plants of these or related crops or on parts of such plants (e.g., fruits, blossoms, foliage, stams, tubers, roots), whereby the newly outgrowing parts of such plants are also protected against fungal attack. The compounds of this invention are active against phytopathogenic fungi belonging to the following classes: Ascomycetes (e.g. Erysiphaceae, Fusarium, Helminthosporium); Basidiomycetes such as particularly rust-fungi (e.g. Puccinia); *Fungi imperfecti* (e.g. Moniliales etc., Cercospora and Botrytis) and Oomycetes belonging to the class of the Phycomycetes such as, for example, Phytophthora and Plasmopara. They can further be used as seed-dressings for the treatment of seed (e.g. fruits, tubers, grains) and cuttings to protect them from fungal infection, and against fungi occuring in the soil.

The application of compounds of formula (I) against microorganisms is intended to be within the scope of the present invention.

Preferred plant-fungicides according to this invention are those compounds of formula (I), including their salts and metal salt complexes, wherein $R^1$ is hydrogen or halo, said substituent being present in the ortho-position; $R^2$ is halo in the para-position and $R^3$ is hydrogen. Especially preferred compounds among the foregoing are those wherein halo represents chloro.

The following examples are intended to illustrate and not to limit the scope of the present invention. Unless otherwise indicated all parts therein are by weight.

A. EXAMPLES OF CHEMICAL PREPARATION

Example I

To 53 parts of 3-methoxy-1,2,-propanediol and 75 parts of (2,4-dichlorophenyl)ethanone, dissolved in 170 parts of methylbenzene are added 2 parts of 4-methylbenzene sulfonic acid and the whole is refluxed for 8 hours using a water-separator. The thus obtained methylbenzene solution is washed with water, dried and evaporated in vacuo. The residue is distilled in vacuo, yielding 100 parts of 2-(2,4-dichlorophenyl)-2-methyl-4-(methoxymethyl)-1,3-dioxolane; bp. 111°–115° C. at 4 mm. pressure.

To 100 parts of 2-(2,4-dichlorophenyl)-2-methyl-4-(methoxymethyl)-1,3-dioxolane in 480 parts of tetrachloromethane are added at 45° C. a few drops of bromine till the reaction starts. Subsequently 19.6 parts of bromine are added dropwise and the whole is stirred for 2 hours at 20° C. The pale yellow solution is washed with a sodium hydrogen carbonate solution, dried and evaporated. A high vacuum distillation yields 65 parts of pure 2-(2,4-dichlorophenyl)-2-(bromomethyl)-4-(methoxymethyl)-1,3-dioxolane; bp. 129°–132° C. at 0.01 mm. pressure.

A mixture of 13 parts of powdered potassium hydroxide (85% purity), 15 parts of 1H-1,2,4-triazole and 165 parts of dimethylsulfoxide is heated at 80° C. for 1 hour. 58 Parts of 2-(2,4-dichlorophenyl)-2-(bromomethyl)-4-(methoxymethyl)-1,3-dioxolane are added and the whole is heated at 150° C. for 12 hours. The reaction mixture is poured onto 1000 parts of water. The product is extracted with 1,1'-oxybisethane. The extract is dried, filtered and evaporated. The residue is distilled under high vacuum yielding pure 1-[2-(2,4-dichlorophenyl)-4-(methoxymethyl)-1,3-dioxolan-2-ylmethyl]-1H-1,2,4-triazole; bp. 161°–168° C. at 0.01 mm. pressure. The product crystallizes on standing, yielding a solid having a melting point of 64°–74° C.

Example II

A mixture of 4.0 parts of potassium hydroxide (85% purity), 4.1 parts of 1H-1,2,4-triazole and 80 parts of methanol is refluxed for 1 hour. The methanol is evaporated. The residue is dissolved in 140 parts of N,N-dimethylformamide and refluxed for 6 hours in the presence of 20.5 parts of 4-([1,1'-biphenyl]-4-yloxymethyl)-2-(bromomethyl)-2-(2,4-dichlorophenyl)-1,3-dioxolane and 2 parts of potassium iodide. After cooling the mixture is poured onto 800 parts of water and extracted twice with 180 parts of ethyl acetate. The organic layer is washed five times with 100 parts of water, dried over anhydric sodium sulfate, filtered and evaporated. Crystallization of the residue from 2-propanol yields 10.2 parts of cis+trans-1-[4-([1,1'-biphenyl]-4-yloxymethyl)-2-(2,4-dichlorophenyl)-1,3-dioxolan-2-ylmethyl]-1H-1,2,4-triazole. The diastereoisomers having respectively melting points of 150°–151° C. and 104°–105° C. are separated by column-chromatography on neutral aluminium oxide with dichloromethane as eluent.

Following the same procedures and using equivalent amounts of the appropriate starting materials the compounds listed in the following tables I, II, III and IV are prepared:

TABLE I (X = oxygen)

| compound No. | $R^1$ | $R^2$ | $R^3$ | $R^4$ | melting point |
|---|---|---|---|---|---|
| 1 | 2-Cl | 4-Cl | H | —CH$_3$ | 64–74° C. |
| 2 | 2-Cl | 4-Cl | H | —C$_2$H$_5$ | oil $n_D^{23}$ = 1.5441 |
| 3 | 2-Cl | 4-Cl | H | —nC$_3$H$_7$ | oil $n_D^{23}$ = 1.5388 |
| 4 | 2-Cl | 4-Cl | H | —iC$_3$H$_7$ | — |
| 5 | 2-Cl | 4-Cl | H | —CH$_2$—CH=CH$_2$ | oil $n_D^{23}$ = 1.5535 |
| 6 | 2-Cl | 4-Cl | 6-Cl | —CH$_3$ | — |
| 7 | H | 4-Cl | H | —CH$_3$ | — |
| 8 | H | 4-Cl | H | —CH$_2$—CH=CH$_2$ | — |
| 9 | H | 4-Cl | H | —nC$_4$H$_9$ | — |
| 10 | H | 4-Cl | H | —CH$_2$—CH$_2$—O—CH$_3$ | — |
| 11 | 2-Cl | 4-Cl | H | —nC$_4$H$_9$ | oil $n_D^{23}$ = 1.5349 |
| 12 | 2-Cl | 4-Cl | H | —CH$_2$—CH$_2$Br | — |
| 13 | 2-Cl | 4-Cl | H | —sCH$_4$H$_9$ | — |
| 14 | 2-Cl | 4-Cl | H | —CH$_2$—CH$_2$—O—CH$_3$ | oil $n_D^{23}$ = 1.5422 |
| 15 | 2-Cl | 4-Cl | H | —CH$_2$—CH$_2$—O—C$_2$H$_5$ | — |
| 16 | 2-Cl | 4-Cl | H | —CH$_2$—CH$_2$—O—CH$_2$—CH$_2$Cl | — |

TABLE I-continued

[Structure: 1,2,4-triazolyl-CH2-C(connected to two O's forming dioxolane with CH2-X-R4)-phenyl(R1,R2,R3)]

(X = oxygen)

| compound No. | R¹ | R² | R³ | R⁴ | melting point |
|---|---|---|---|---|---|
| 17 | 2-Cl | 4-Cl | H | —CH₂—CH₂Cl | — |
| 18 | 2-Cl | 4-Cl | H | —CH₂—C≡CH | — |
| 19 | 2-Cl | 4-Cl | H | —CH=CH—CH₃ | — |
| 20 | 2-Cl | 4-Cl | H | —nC₅H₁₁ | — |
| 21 | 2-Cl | 4-Cl | H | —(CH₂)₅—CH₃ | — |
| 22 | 2-Cl | 4-Cl | H | —(CH₂)₆—CH₃ | — |
| 23 | 2-Cl | 4-Cl | H | —(CH₂)₉—CH₃ | — |
| 24 | 2-Cl | 4-Cl | H | —(CH₂)₁₁—CH₃ | — |
| 25 | 2-Cl | 4-Cl | H | cyclohexyl | — |
| 26 | 2-Cl | 4-Cl | H | phenyl | 88–90° C. |
| 27 | 2-Cl | 4-Cl | H | 3,5-dichlorophenyl | 93.5–96° C. |
| 28 | 2-Cl | 4-Cl | H | 4-chlorophenyl | 116.5–120° C. |
| 29 | 2-Cl | 4-Cl | H | 4-methylphenyl | 126–130° C. |
| 30 | 2-Cl | 4-Cl | H | 4-Cl-3-CH₃-phenyl | — |
| 31 | 2-Cl | 4-Cl | H | 4-Cl-3-CH₃-phenyl | 88.5–92 |
| 32 | 2-Cl | 4-Cl | H | —CH₂—phenyl | — |
| 33 | 2-Cl | 4-Cl | H | —CH₂—(4-Cl-phenyl) | — |
| 34 | 2-Cl | 4-Cl | H | —CH₂—(4-NO₂-phenyl) | — |
| 35 | 2-Cl | 4-Cl | H | 2-OCH₃-phenyl | — |
| 36 | 2-Br | 4-Br | 6-Br | —CH₃ | — |
| 37 | 2-Cl | 4-Cl | H | 4-Br-phenyl | — |
| 38 | 2-Cl | 4-Cl | H | biphenyl | A-isomer 150–151° C. |
| 39 | 2-Cl | 4-Cl | H | biphenyl | B-isomer 104–105° C. |
| 40 | 2-Cl | 4-Cl | H | 4-phenoxyphenyl | 109–111° C. |
| 41 | H | H | H | —C₂H₅ | — |
| 42 | 2-CH₃ | 4-Cl | H | —C₂H₅ | — |
| 43 | H | 3NO₂ | H | —C₂H₅ | — |
| 44 | H | H | H | —CH₃ | — |

TABLE I-continued

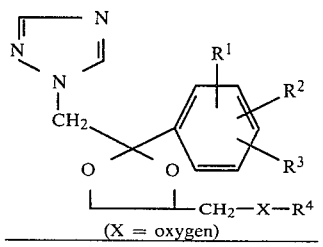
(X = oxygen)

| compound No. | R¹ | R² | R³ | R⁴ | melting point |
|---|---|---|---|---|---|
| 45 | H | 3NO₂ | H | —CH₂—CH₂—O—CH₃ | — |
| 46 | H | 3CN | H | —C₂H₅ | — |
| 47 | H | H | H | —CH₂—CH₂—O—CH₃ | — |
| 48 | 2-CH₃ | 4-Cl | H | —CH₃ | — |
| 49 | 2-CH₃ | 4-Cl | H | —CH₂—CH₂—O—C₂H₅ | — |
| 50 | 2-OC₂H₅ | 4-Cl | H | —C₂H₅ | — |
| 51 | 2-OC₂H₅ | 4-Cl | H | —CH₃ | — |
| 52 | 2-OC₂H₅ | 4-Cl | H | —CH₂—CH₂—O—CH₃ | — |
| 53 | 2-Cl | 6-Cl | H | —C₂H₅ | — |

TABLE II
(X = sulfur)

| Compound No | R¹ | R² | R³ | R⁴ | melting point |
|---|---|---|---|---|---|
| 54 | 2-Cl | 4-Cl | H | —CH₃ | — |
| 55 | 2-Cl | 4-Cl | H | —C₂H₅ | — |
| 56 | 2-Cl | 4-Cl | H | —nC₃H₇ | — |
| 57 | 2-Cl | 4-Cl | H | —nC₄H₇ | — |
| 58 | 2-Cl | 4-Cl | H | —iC₃H₇ | — |
| 59 | 2-Cl | 4-Cl | H | —nC₈H₁₇ | — |
| 60 | 2-Cl | 4-Cl | H | —CH₂—CH=CH₂ | — |
| 61 | 2-Cl | 4-Cl | H | —⟨H⟩ (cyclohexyl) | — |
| 62 | 2-Cl | 4-Cl | H | —⟨phenyl⟩-Cl | — |
| 63 | 2-Cl | 4-Cl | H | —⟨phenyl⟩-CH₃ | — |
| 64 | 2-Cl | 4-Cl | H | —CH₂—⟨phenyl⟩ | — |
| 65 | 2-Cl | 2-Cl | H | —CH₂—⟨phenyl⟩-Cl | — |
| 66 | H | 4-Cl | H | —CH₃ | — |
| 67 | 2-Cl | 4-Cl | 6-Cl | —CH₃ | — |
| 68 | 2-Cl | 6-Cl | H | —CH₃ | — |
| 69 | H | H | H | —C₂H₅ | — |
| 70 | H | 3-NO₂ | H | —CH₂—CH₂O—CH₃ | — |
| 71 | 2-OC₂H₅ | 4-Cl | H | —C₂H₅ | — |
| 72 | 2-iC₃H₇ | 4-Cl | H | —CH₂—CH₂OC₂H₅ | — |

TABLE III
(X = oxygen)

| Compound No. | Salt | R¹ | R² | R³ | R⁴ | melting point |
|---|---|---|---|---|---|---|
| 73 | HNO₃ | H | 2-Cl | H | —CH₃ | — |
| 74 | CuCl₂ | 2-Cl | 4-Cl | H | —CH₃ | — |
| 75 | ZnCl₂ | 2-Cl | 4-Cl | H | —⟨phenyl⟩ | — |
| 76 | HCl | 2-Cl | 4-Cl | H | —CH₂CH=CH₂ | — |
| 77 | Mn(NO₃)₂ | 2-Cl | 4-Cl | H | —⟨biphenyl⟩ | — |
| 78 | (COOH)₂ | 2-Cl | 4-Cl | H | —CH₂—⟨phenyl⟩ | — |

TABLE IV
(X = sulfur)

| Compound No. | Salt | R¹ | R² | R³ | R⁴ | melting point |
|---|---|---|---|---|---|---|
| 79 | HNO₃ | 2-Cl | 4-Cl | H | —CH₃ | — |
| 80 | (Z)-2-butenedioate | 2-Cl | 4-Cl | H | —C₂H₅ | — |
| 81 | HCl | 2-Cl | 4-Cl | H | —nC₄H₉ | — |
| 82 | FeCl₃ | 2-Cl | 4-Cl | H | —CH₂CH=CH₂ | — |

Example III

A mixture of 4.6 parts of 1,2,3-propanetriol, 2 parts of 4-methylbenzenesulfonic acid, 40 parts of butanol and 225 parts of methylbenzene is distilled azeotropically to dry. Then there are added 7 parts of 1-[2-(2,4-dichlorophenyl)-2,2-dimethoxyethyl]-1H-1,2,4-triazole and the whole is stirred and refluxed for 3 days with water-separator. The reaction mixture is cooled, stirred with a sodium hydroxide solution 20% and poured onto water. The product is extracted with 2,2'-oxybispropane. The extract is washed with water, dried, filtered and evaporated. The residue is crystallized from 4-methyl-2-pentanone and 2,2'-oxybispropane. The product is filtered off and dried, yielding 2.7 parts (54%) of (A+B)-2-(2,4-dichlorophenyl)-2-(1H-1,2,4-triazol-1-ylmethyl)-1,3-dioxolane-4-methanol; mp. 103.3° C.

Example IV

To a stirred mixture of 2.2 parts of iodomethane, 3.9 parts of cis-2-(2,4-dichlorophenyl)-2-(1H-1,2,4-triazol-1-ylmethyl)-1,3-dioxolane-4-methanol and 90 parts of N,N-dimethylformamide are added 0.5 parts of sodium hydride dispersion 76%. The whole is stirred for 3 hours at room temperature. The reaction mixture is poured onto water and the product is extracted with 2,2'-oxybispropane. The extract is washed with water, dried, filtered and the filtrate is acidified with nitric acid. The formed nitrate salt is filtered off and crystallized from 4-methyl-2-pentanone, yielding 2.1 parts of cis-1-[2-(2,4-dichlorophenyl)-4-(methoxymethyl)-1,3-dioxolan-2-ylmethyl]-1H-1,2,4-triazole mononitrate; mp. 140° C. (compound 83).

Example V

Following the procedure of Example IV and using equivalent amounts of the appropriate starting materials there are also prepared:

cis-1-[2-(2,4-dichlorophenyl)-4-(ethoxymethyl)-1,3-dioxolan-2-ylmethyl]-1H-1,2,4-triazole mononitrate; mp. 146.9° C. (compound 84);

cis-1-[2-(2,4-dichlorophenyl)-4-(propoxymethyl)-1,3-dioxolan-2-ylmethyl]-1H-1,2,4-triazole mononitrate; mp. 136° C. (compound 85);

cis-1-[4-(butoxymethyl)-2-(2,4-dichlorophenyl)-1,3-dioxolan-2-ylmethyl]-1H-1,2,4-triazole mononitrate; mp. 128.6° C. (compound 86);

cis-1-[2-(2,4-dichlorophenyl)-4-(pentyloxymethyl)-1,3-dioxolan-2-ylmethyl]-1H-1,2,4-triazole mononitrate; mp. 110.3° C.; (compound 87);

cis-1-[2-(2,4-dichlorophenyl)-4-(hexyloxymethyl)-1,3-dioxolan-2-ylmethyl]-1H-1,2,4-triazole mononitrate; mp. 103.8° C. (compound 88);

cis-1-[2-(2,4-dichlorophenyl)-4-(heptyloxymethyl)-1,3-dioxolan-2-ylmethyl]-1H-1,2,4-triazole mononitrate; mp. 104.7° C.; (compound 89);

cis-1-[2-(2,4-dichlorophenyl)-4-(2-propenyloxymethyl)-1,3-dioxolan-2-ylmethyl]-1H-1,2,4-triazole mononitrate; mp. 173.3° C. (compound 90);

cis-1-[2-(2,4-dichlorophenyl)-4-(2-propynyloxymethyl)-1,3-dioxolan-2-ylmethyl]-1H-1,2,4-triazole mononitrate; mp. 116.6° C. (compound 91);

cis-1-[2-(2,4-dichlorophenyl-4-(2-propynyloxymethyl)-1,3-dioxolan-2-ylmethyl]-1H-1,2,4-triazole; mp. 84.7° C. (compound 92);

cis-1-{4-[(4-chlorophenyl)methoxymethyl]-2-(2,4-dichlorophenyl)-1,3-dioxolan-2-ylmethyl}-1H-1,2,4-triazole mononitrate; mp. 133° C. (compound 93);

cis-1-[2-(2,4-dichlorophenyl)-4-(3-phenyl-2-propenyloxymethyl)-1,3-dioxolan-2-ylmethyl]-1H-1,2,4-triazole ethanedioate (1:1); mp. 114.1° C. (compound 94);

cis-1-[2-(2,4-dichlorophenyl)-4-(phenylmethoxymethyl)-1,3-dioxolan-2-ylmethyl]-1H-1,2,4-triazole mononitrate; mp. 100.8° C. (compound 95);

cis-1-{2-(2,4-dichlorophenyl)-4-[(2,4-dichlorophenyl)methoxymethyl]-1,3-dioxolan-2-ylmethyl}-1H-1,2,4-triazole mononitrate; mp. 135.9° C. (compound 96); and cis-1-[2-(2,4-dichlorophenyl)-4-{[(4-methoxyphenyl)methoxy]methyl}-1,3-dioxolan-2-ylmethyl]-1H-1,2,4-triazole mononitrate; mp. 134.8° C. (compound 97).

Example VI

To a stirred sodium methoxide solution, prepared starting from 1.2 parts of sodium in 56 parts of methanol, are added 3.4 of 1H-1,2,4-triazole and 135 parts of N,N-dimethylformamide. The methanol is distilled off at normal pressure till internal temperature of 135° C. After the addition of 15 parts of A-2-(bromomethyl)-4-(4-bromophenoxymethyl)-2-(2,4-dichlorophenyl)-1,3-dioxolane, the whole is stirred and refluxed overnight. The reaction mixture is allowed to cool to room temperature and poured onto water. The precipitated product is filtered off and dissolved in trichloromethane. This solution is dried, filtered and evaporated. The residue is purified by column-chromatography over silica gel using trichloromethane as eluent. The pure fractions are collected and the eluent is evaporated. The residue is triturated in 2,2'-oxybispropane. The product is filtered off and dried, yielding 10.8 parts (74%) of A-1-[4-(4-bromophenoxymethyl)-2-(2,4-dichlorophenyl)-1,3-dioxolan-2-ylmethyl]-1H-1,2,4-triazole; mp. 149.1° C. (compound 98).

In a similar manner there is also prepared:

(A+B)-1-[2-(2,4-dichlorophenyl)-4-ethenyl-1,3-dioxolan-2-ylmethyl]-1H-1,2,4-triazole nitrate hemihydrate; mp. 91.2° C. (compound 99).

Example VII

A mixture of 6.3 parts of 1H-1,2,4-triazole, 7.5 parts of (cis+trans)-2-(bromomethyl)-2-(4-bromophenyl)-4-(2,4-dichlorophenyl)-1,3-dioxolane, 5 parts of sodium carbonate and 90 parts of N,N-dimethylformamide is stirred for 48 hours at reflux temperature. The reaction mixture is cooled and poured onto water. The product is extracted twice with benzene. The combined extracts are dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in 4-methyl-2-pentanone and 2,2'-oxybispropane. The salt is filtered off and crystallized from 4-methyl-2-pentanone, yielding 4.5 parts (95%) of (cis+trans)-1-[2-(4-bromophenyl)-4-(2,4-dichlorophenyl)-1,3-dioxolan-2-ylmethyl]-1H-1,2,4-triazole ethanedioate (2:3); mp. 183.2° C. (compound 100).

In a similar manner there are also prepared:

(cis+trans)-1-[4-(4-chlorophenylmethyl)-2-(2,4-dichlorophenyl)-1,3-dioxolan-2-ylmethyl]-1H-1,2,4-triazole ethanedioate (2:3); mp. 123.9° C. (compound 101).

(cis+trans)-1-[2-(2,4-dichlorophenyl)-4-(4-methylphenylmethyl)-1,3-dioxolan-2-ylmethyl]-1H-1,2,4-triazole ethanedioate(2:3); mp. 142.9° C. (compound 102);

(cis+trans)-1-[2-(2,4-dichlorophenyl)-4-(2-phenylethyl)-1,3-dioxolan-2-ylmethyl]-1H-1,2,4-triazole ethanedioate (2:3) monohydrate; mp. 92.1° C. (compound 103).

Example VIII

To a stirred sodium methoxide solution, prepared starting from 0.3 parts of sodium and 56 parts of methanol, are added 8.9 parts of 1H-1,2,4-triazole and 180 parts of N,N-dimethylformamide. 120 Parts of solvent are distilled off while stirring. Then there are added 21.3 parts of A+B-4-([1,1'-biphenyl]-4-yloxymethyl)-2-(bromomethyl)-2-(2,4-dichlorophenyl)-1,3-dioxolane. After stirring for 6 hours at reflux, the reaction mixture is allowed to cool to room temperature, poured onto water and the product is extracted three times with 1,1'-oxybisethane. The combined extracts are washed twice with water, dried, filtered and evaporated. The residue is purified by column-chromatography over silica gel using trichloromethane as eluent. The first fraction (A=cis-isomer) is collected and the eluent is evaporated. The residue is crystallized from acetonitrile, yielding 6.5 parts (31%) of cis-1-[4-([1,1'-biphenyl]-4-yloxymethyl)-2-(2,4-dichlorophenyl)-1,3- dioxolan-2-ylmethyl]-1H-1,2,4-triazole; mp. 156.5° C. (compound 38).

The second fraction (B=trans-isomer) is collected and the eluent is evaporated. The residue is crystallized from 1,1'-oxybisbutane, yielding 5.1 parts of trans-1-[4-([1,1'-biphenyl]-4-yloxymethyl)-2-(2,4-dichlorophenyl)-1,3-dioxolan-2-ylmethyl]-1H-1,2,4-triazole; mp. 110.4° C. (compound 39).

Example IX

A mixture containing 9 parts of potassium carbonate, 4.5 parts of 1H-1,2,4-triazole, 19.2 parts of 2-(2-bromomethyl)-2-(2,4-dichlorophenyl)-4-[(1-methylethoxy)methyl]-1,3-dioxolane, 0.2 parts of sodium iodide and 100 parts of dimethylsulfoxide is mixed during 20 hours at 100° C. After cooling the mixture is poured in 600 parts of water and the aqueous solution is extracted three times with 200 parts of ethyl acetate. The combined ethyl acetate layers are washed with 200 parts of water, dried, filtered and evaporated. The residual oil, containing a diastereomeric mixture of 1-[2-(2,4-dichlorophenyl)-4-[(1-methylethoxy)methyl]-1,3-dioxolan-2-ylmethyl]-1H-1,2,4-triazole, is purified by column-chromatography over silica gel using ethyl acetate as eluent. The combined fractions 4 to 7 yield, after evaporation of the ethyl acetate, the cis-isomer, $n_D^{22}=1.5383$, and the combined fractions 10 to 17 yield, after evaporation, the trans-isomer, mp. 50.5°–53° C. (compounds 104 and 105 respectively).

Example X

A mixture of 3.8 parts of 4-bromobenzenethiol, 8 parts of cis-[2-(2,4-dichlorophenyl)-2-(1H-1,2,4-triazol-1-ylmethyl)-1,3-dioxolan-4-ylmethyl] methanesulfonate, 0.8 parts of sodium hydroxide and 80 parts of methanol is stirred first for 5 hours at reflux and further overnight at room temperature. The reaction mixture is poured onto water and the product is extracted three times with dichloromethane. The combined extracts are washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in 4-methyl-2-pentanone. The salt is filtered off and crystallized from a mixture of 2,2'-oxybispropane and methanol, yielding 6.2 parts of cis-1-[4-(4-bromophenylthiomethyl)-2-(2,4-dichlorophenyl)1,3-dioxolan-2-ylmethyl]-1H-1,2,4-triazole ethanedioate (1:1); mp. 130.1° C. (compound 106).

Following the same procedure and using equivalent amounts of the appropriate starting materials there are also prepared:

cis-1-[4-(4-chlorophenylthiomethyl)-2-(2,4-dichlorophenyl)-1,3-dioxolan-2-ylmethyl]-1H-1,2,4-triazole ethanedioate (1:1); mp. 138.2° C. (compound 107);

cis-1-[4-(4-methoxyphenylthiomethyl)-2-(2,4-dichlorophenyl)-1,3-dioxolan-2-ylmethyl]-1H-1,2,4-triazole; mp. 96.4° C. (compound 108);

cis-1-[2-(2,4-dichlorophenyl)-4-(phenylthiomethyl)-1,3-dioxolan-2-ylmethyl]-1H-1,2,4-triazole ethanedioate (1:1) mp. 136.9° C. (compound 109);

cis-1-[4-(butylthiomethyl)-2-(2,4-dichlorophenyl)-1,3-dioxolan-2-ylmethyl]-1H-1,2,4-triazole ethanedioate (1:1); mp. 135.1° C.; (compound 110); and cis-1-[2-(2,4-dichlorophenyl)-4-(heptylthiomethyl)-1,3-dioxolan-2-ylmethyl]-1H-1,2,4-triazole ethanedioate (1:1); mp. 140.4° C. (compound 111).

Example XI

To a stirred mixture of 3.3 parts of iodine, 4.4 parts of cis-1-[2-(2,4-dichlorophenyl)-4-(2-propynyloxymethyl)-1,3-dioxolan-2-ylmethyl]-1H-1,2,4-triazole and 70 parts of methanol are added 15 parts of sodium hydroxide solution 10% at room temperature. Stirring at room temperature is continued for 2 hours. The reaction mixture is poured onto water and the product is extracted with 1,1'-oxybisethane. The extract is washed with water, dried, filtered and evaporated. The residue is crystallized from 4-methyl-2-pentanone. The product is filtered off and dried in vacuo at room temperature, yielding 0.8 parts of cis-1-[2-(2,4-dichlorophenyl)-4-(3-iodo-2-propynyloxymethyl)-1,3-dioxolan-2-ylmethyl]-1H-1,2,4-triazole; mp. 124.1° C. (compound 112).

B. FORMULATION EXAMPLES

Example XII

Dusts: The following substances are used to prepare (a) 5% and (b) a 2% dust:

| (a) | 5 parts of active substance |
| | 95 parts of talc; |
| (b) | 2 parts of active substance |
| | 1 part of highly dispersed silicic acid |
| | 97 parts of talc. |

The active substances are mixed with the carriers and ground and in this form can be processed to dusts for application.

Example XIII

Granulate: The following substances are used to prepare a 5% granulate:

| 5 parts of active substance |
| 0.25 part of epichlorohydrin |
| 0.25 part of cetyl polyglycol ether |
| 3.25 parts of polyethylene glycol |
| 91 parts of kaolin (particle size 0.3–0.8 mm.). |

The active substance is mixed with epichlorohydrin and the mixture is dissolved in 6 parts of 2-propanone. Then polyethylene glycol and cetyl polyglycol ether are added. The resultant solution is sprayed on kaolin and the 2-propanone is evaporated in vacuo. Such a microgranulate is advantageously used for combating soil fungi.

Example XIV

Wettable powders: The following constituents are used to prepare (a) a 70%, (b) a 40%, (c) and (d) a 25% and (e) a 10% wettable powder:

| (a) | 70 parts of active substance |
| | 5 parts of sodium dibutylnaphthylsulfonate |
| | 3 parts of naphthalenesulfonic acid/phenolsulfonic acid/formaldehyde condensate (3:2:1). |
| | 10 parts of kaolin |
| | 12 parts of Champagne chalk. |
| (b) | 40 parts of active substance |
| | 5 parts of sodium ligninsulfonate |
| | 1 part of sodium dibutylnaphthalenesulfonic acid |
| | 54 parts of silicic acid. |

| | | |
|---|---|---|
| (c) | 25 | parts of active substance |
| | 4.5 | parts of calcium ligninsulfonate |
| | 1.9 | parts of Champagne chalk/hydroxyethyl cellulose mixture (1:1) |
| | 1.5 | parts of sodium dibutylnaphthalenesulfonate |
| | 19.5 | parts of silicic acid |
| | 19.5 | parts of Champagne chalk |
| | 28.1 | parts of kaolin |
| (d) | 25 | parts of active substance |
| | 2.5 | parts of isooctylphenoxy-polyethylene-ethanol |
| | 1.7 | parts of a Champagne chalk/hydroxyethyl cellulose mixture (1:1) |
| | 8.3 | parts of a sodium aluminium silicate |
| | 16.5 | parts of kieselguhr |
| | 46 | parts of kaolin |
| (e) | 10 | parts of active substance |
| | 3 | parts of a mixture of the sodium salts of saturated fatty alcohol sulfates |
| | 5 | parts of naphthalenesulfonic acid/formaldehyde condensate |
| | 82 | parts of kaolin. |

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

Example XV

Emulsifiable concentrates: the following substances are used to prepare a 25% emulsifiable concentrate:

| | |
|---|---|
| 25 | parts of active substance |
| 2.5 | parts of epoxidised vegetable oil |
| 10 | parts of an alkylarylsulfonate/fatty alcohol polyglycol ether mixture |
| 5 | parts of dimethyl formamide |
| 57.5 | parts of dimethylbenzene. |

By diluting such a concentrate with water it is possible to prepare emulsions of the desired concentration, which are especially suitable for leaf application.

C. BIOLOGICAL EXAMPLES

Example XVI

Activity against Cercospora arachidicola on ground-nut plants

Ground-nut plants, between 10 cm and 15 cm in height, are sprayed with a spray broth (containing 0.02% of active substance) prepared from a wettable powder of the active substance. After about 48 hours the treated plants are infected by dusting them with a suspension of conidia of the fungus. The infected plants are then incubated for about 72 hours at 21° C. and at high relative humidity and then stood in the glass-house. Fungal infection is evaluated 12 days after the day of infection on basis of the number and the extend of the appearing spots.

Example XVII

Activity against Plasmopara viticola on grapevines

Grapevine seedlings, having 4–5 leaves, are sprayed with a spray broth (containing 0.06% of active substance) prepared from a wettable powder of the active substance. After about 24 hours the treated plants are infected with a suspension of sporangia of the fungus. Fungal attack is evaluated after incubating the plants for 6 days at 95°–100° C. relative humidity and at 20° C.

Example XVIII

Activity against Erysiphe graminis on barley

Residual protective action

Barley plants, about 8 cm in height, are sprayed with a spray broth (containing 0.02% of active substance) prepared from a wettable powder of the active substance. After 3–4 hours the treated plants are dusted with conidia of the fungus. The infected barley plants are then placed in a glass-house at about 22° C. and fungal attack is evaluated. 10 days after the day of infection.

Systemic action

A spray broth (containing 0.006% of the active substance; the amount being proportional with the soil-volume), prepared from a wettable powder of the active substance is administered to barley plants, about 8 cm in height, while care is taken that the external parts of the plants do not enter into contact with the spray. After 48 hours the treated plants are dusted with conidia of the fungus. The infected barley-plants are stood in a glass-house at 22° C. and the fungal infection is evaluated after 10 days.

Example XIX

Activity against Hemileia vastatrix on coffee-trees

Residual protective action

Coffee-trees, about 15 cm in height, are sprayed with a spray broth (containing 0.02% of active substance) prepared from a wettable powder of the active substance. After 24 hours the treated plants are infected with a suspension of spores of the rust fungus. The infected coffee-plants are stood in a humidity room during 96 hours and then in a glass-house at 22° C. until the appearance of rust-pustules. The reduction of the number of rust-pustules is a measure for the activity of the test substances.

Example XX

Activity against Veturia inaequalis on apple seedlings

Residual protective action

Apple seedlings, having about 5 developped leaves, are sprayed with a spray broth (containing 0.06% of active substance) prepared from a wettable powder of the active substance. After 24 hours the treated plants are infected with a suspension of conidia of the fungus. The plants are then incubated at 90–100% relative humidity and subsequently they are stood in a glass-house at 20°–24° C. The fungal infection is evaluated 15 days after the day of infection.

EXAMPLE XXI

Activity against Puccinia graminis on wheat

Residual protective action

Wheat plants where sprayed 6 days after sowing with a spray broth (0.06% of active substance) prepared from a wettable powder of the active substance. After 24 hours the treated plants were infected with a suspension of Uredospores of the fungus. After an incubation period of 48 hours at 95–100% relative humidity and at about 20° C. the plants were stood in a greenhouse at approx. 22° C. The development of rust-pustules was evaluated 12 days after the infection.

Systemic action

5 Days after sowing wheat plants are sprayed with a spray broth (containing 0.006% of active substance; the amount of the spray being proportional with the soil-volume) prepared from a wettable powder of the active substance. After 48 hours the treated plants are infected with a suspension of Uredospores of the fungus. After an incubation period of 48 hours at 95–100% relative humidity and at 20° C. the treated plants are stood in a glass-house at about 22° C. The rust-pustules are evaluated 12 days after the day of infection.

EXAMPLE XXII

Activity against Botrytis cinerea on broad beans

Broad bean plants, about 10 cm in height, are sprayed with a spray broth (containing 0.02% of active substance) prepared from a wettable powder of the active substance. After 48 hours the treated plants are infected with a suspension of conidia of the fungus. After incubating the infected plants for 2–3 days at 95–100% relative humidity and at 21° C. the fungal infection is evaluated.

EXAMPLE XXIII

Activity against Podosphoera leucotricha on apple seedlings

Residual protective action

Apple seedlings, having about 5 developed leaves, are sprayed with a spray broth (containing 0.06% active substance) prepared from a wettable powder of the active substance. After 24 hours the treated plants are infected with a suspension of conidia of the fungus and the infected plants are stood in growth-chamber at 70% relative humidity and at 20° C. The fungal infection is evaluated 12 days after the day of infection.

In the foregoing tests, evaluations are expressed as percent infection of treated plants compared with untreated, infected control plants (=100% infection).

The compounds of formula (I) display good fungicidal activity in one or more of the abovedescribed tests.

The substances listed hereafter were found to reduce infection by the following fungi to less than 20%.

| | |
|---|---|
| *Cercospora arachidicola:* | 1, 2, 3, 5, 11, 14, 26, 37 and 40 |
| *Plasmopara viticola:* | 5 and 11 |
| *Erysiphe granimis:* | 1, 2, 3, 5, 11, 14, 26, 37 and 38 |
| *Hemileia vastatrix:* | 1 |
| *Venturia inaequalis:* | 1, 2, 3, 5, 11, 14 and 26 |
| *Puccinia granimis:* | 1, 2, 3, 5, 11, 14 and 26 |
| *Botrytis cinerea:* | 1 and 5 |
| *Podosphaera leucotricha:* | 1, 2, 3, 5, 11, 14, 26 and 37. |

What is claimed is:

1. A chemical compound selected from the group consisting of a 1H-1,2,4-triazole derivative having the formula:

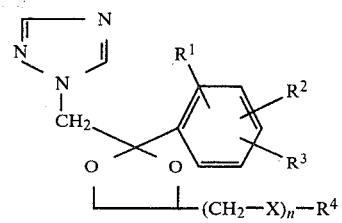

and the phytopharmaceutically acceptable acid addition salts and stereochemically isomeric forms thereof, wherein:

$R^1$, $R^2$ and $R^3$ are each independently selected from the group consisting of hydrogen, lower alkyl, lower alkyloxy, halo, nitro, cyano and trifluoromethyl;

n is the integer 0 or 1;

X is a member selected from the group consisting of O and S; and $R^4$ is a member selected from the group consisting of alkyl, mono-, di- and trihaloalkyl, lower alkyloxy-lower alkyl, mono-, di- and trihalolower alkyloxy-lower alkyl, lower alkenyl, 2-propynyl, 3-halo-2-propynyl, cycloakyl, aryl, aryllower alkyl and aryl-lower alkenyl, wherein said aryl is selected from the group consisting of phenyl and substituted phenyl, said substituted phenyl having from 1 to 3 substituents each independently selected from the group consisting of lower alkyl, lower alkyloxy, halo, nitro, cyano, trifluoromethyl, phenyl, phenyloxy and phenylthio, provided that only one of the substituents may be selected from the group consisting of phenyl, phenyloxy and phenylthio, and wherein said phenyl and the phenyl part of said phenoxy and phenylthio are optionally substituted with up to three substituents each independently selected from the group consisting of lower alkyl, lower alkyloxy, halo, nitro, cyano and trifluoromethyl, provided that when n is 0 then $R^4$ is other than alkyl, and wherein said alkyl, used as such or as part of another substituent, is selected from straight and branched hydrocarbon radicals having from 1 to 12 carbon atoms and said cycloalkyl is selected from cyclopropyl, cyclobutyl, cyclopentyl, and cyclohexyl.

2. A compound selected from the group consisting of 1-[2-(2,4-dichlorophenyl)-4-(methoxymethyl)-1,3-dioxolan-2-ylmethyl]-1H-1,2,4-triazole and the phytopharmaceutically acceptable acid addition salts and stereochemically isomeric forms thereof.

3. A compound selected from the group consisting of 1-[2-(2,4-dichlorophenyl)-4-(ethoxymethyl)-1,3-dioxolan-2-ylmethyl]-1H-1,2,4-triazole and the phytopharmaceutically acceptable acid addition salts and stereochemically isomeric forms thereof.

4. A compound selected from the group consisting of 1-[2-(2,4-dichlorophenyl)-4-(propoxymethyl)-1,3-dioxolan-2-ylmethyl]-1H-1,2,4-triazole and the phytopharmaceutically acceptable acid addition salts and stereochemically isomeric forms thereof.

5. A compound selected from the group consisting of 1-[2-(2,4-dichlorophenyl)-4-(2-propenyloxymethyl)-1,3-dioxolan-2-ylmethyl]-1H-1,2,4-triazole and the phytopharmaceutically acceptable acid addition salts and stereochemically isomeric forms thereof.

6. A compound selected from the group consisting of 1-[4-(butoxymethyl)-2-(2,4-dichlorophenyl)-1,3-dioxolan-2-ylmethyl]-1H-1,2,4-triazole and the phytopharmaceutically acceptable acid addition salts and stereochemically isomeric forms thereof.

7. A compound selected from the group consisting of 1-{2-(2,4-dichlorophenyl)-4-[(2-methoxyethoxy)methyl]-1,3-dioxolan-2-ylmethyl}-1H-1,2,4-triazole and the phytopharmaceutically acceptable acid addition salts and stereochemically isomeric forms thereof.

8. A compound selected from the group consisting of 1-[-2-(2,4-dichlorophenyl)-4-(phenoxymethyl)-1,3-dioxolan-2-ylmethyl]-1H-1,2,4-triazole and the phytopharmaceutically acceptable acid addition salts and stereochemically isomeric forms thereof.

9. A compound selected from the group consisting of 1-{4-[(4-bromophenoxy)methyl]-2-(2,4-dichlorophenyl)-1,3-dioxolan-2-ylmethyl}-1H-1,2,4-triazole and the phytopharmaceutically acceptable acid addition salts and stereochemically isomeric forms thereof.

10. A compound selected from the group consisting of cis-1-[4-([1,1'-biphenyl]-4-yloxymethyl)-2-(2,4-dichlorophenyl)-1,3-dioxolan-2-ylmethyl]-1H-1,2,4-triazole and the phytopharmaceutically acceptable acid addition salts and stereochemically isomeric forms thereof.

11. A composition for combatting a fungus comprising an inert carrier material and as an active ingredient an effective amount of a compound selected from the group consisting of a 1H-1,2,4-triazole derivative having the formula:

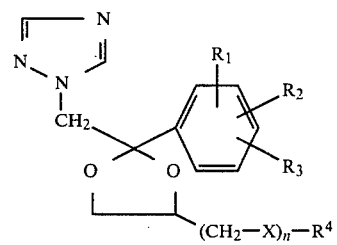

and the phytopharmaceutically acceptable acid addition salts and stereochemically isomeric forms thereof, wherein;

$R^1$, $R^2$ and $R^3$ are each independently selected from the group consisting of hydrogen, lower alkyl, lower alkyloxy, halo, nitro, cyano and trifluoromethyl;

n is the integer 0 or 1;

X is a member selected from the group consisting of O and S; and $R^4$ is a member selected from the group consisting of alkyl, mono-, di- and thrihalo-alkyl, lower alkyloxy-lower alkyl, mono-, di- and trihalo-lower alkyloxy-lower alkyl, lower alkenyl, 2-propynyl, 3-halo-2-propynyl, cycloalkyl, aryl, aryl-lower alkyl and aryllower alkenyl, wherein said aryl is selected from the group consisting of phenyl and substituted phenyl, said substituted phenyl having from 1 to 3 substituents each independently selected from the group consisting of lower alkyl, lower alkyloxy, halo, nitro, cyano, trifluoromethyl, phenyl, phenyloxy and phenylthio, provided that only one of the substituents may be selected from the group consisting of phenyl, phenyloxy and phenylthio, and wherein said phenyl and the phenyl part of said phenoxy and phenylthio are optionally substituted with up to three substituents each independently selected from the group consisting of lower alkyl, lower alkyloxy, halo, nitro, cyano and trifluoromethyl, provided that when n is 0 then $R^4$ is other than alkyl, and wherein said alkyl, used as such or as part of another substituent, is selected from straight and branched hydrocarbon radicals having from 1 to 12 carbon atoms and said cycloalkyl is selected from cyclopropyl, cyclobutyl, cyclopentyl, and cyclohexyl.

* * * * *